(12) United States Patent
Brousmiche et al.

(10) Patent No.: US 9,772,333 B2
(45) Date of Patent: Sep. 26, 2017

(54) RAPID FLUORESCENCE TAGGING OF GLYCANS AND OTHER BIOMOLECULES WITH ENHANCED MS SIGNALS

(71) Applicant: Waters Technologies Corporation, Milford, MA (US)

(72) Inventors: Darryl W. Brousmiche, Grafton, MA (US); Ying-Qing Yu, Uxbridge, MA (US)

(73) Assignee: Water Technologies Corporation, Milford, MA (US)

( * ) Notice: Subject to any disclaimer, the term of this patent is extended or adjusted under 35 U.S.C. 154(b) by 637 days.

(21) Appl. No.: 14/193,418

(22) Filed: Feb. 28, 2014

(65) Prior Publication Data

US 2014/0179011 A1 Jun. 26, 2014

Related U.S. Application Data

(63) Continuation of application No. PCT/US2012/057996, filed on Sep. 28, 2012.

(60) Provisional application No. 61/540,306, filed on Sep. 28, 2011.

(51) Int. Cl.
*G01N 33/00* (2006.01)
*G01N 33/58* (2006.01)
*C07D 207/46* (2006.01)

(52) U.S. Cl.
CPC ........... *G01N 33/58* (2013.01); *C07D 207/46* (2013.01); *G01N 33/582* (2013.01); *G01N 2400/00* (2013.01); *G01N 2400/12* (2013.01); *G01N 2458/15* (2013.01); *G01N 2458/20* (2013.01); *Y10T 436/143333* (2015.01)

(58) Field of Classification Search
CPC ..................................................... G01N 33/58
USPC ........................................................ 436/89
See application file for complete search history.

(56) References Cited

U.S. PATENT DOCUMENTS

| | | | |
|---|---|---|---|
| 4,003,912 | A | 1/1977 | Franz |
| 5,296,599 | A | 3/1994 | Cohen et al. |
| 6,245,478 | B1 | 6/2001 | Uetani et al. |
| 6,632,629 | B2 | 10/2003 | Yang et al. |
| 7,148,069 | B2 | 12/2006 | Miyano et al. |
| 7,494,815 | B2 | 2/2009 | Shimbo et al. |
| 8,124,792 | B2 | 2/2012 | Baginski |
| 2001/0026929 | A1 | 10/2001 | Yang et al. |
| 2005/0079624 | A1 | 4/2005 | Miyano et al. |
| 2005/0158708 | A1 | 7/2005 | Alroy et al. |
| 2006/0286673 | A1 | 12/2006 | Miyano et al. |
| 2008/0241856 | A1 | 10/2008 | Wong et al. |
| 2008/0315084 | A1 | 12/2008 | Yamada et al. |
| 2009/0258437 | A1 | 10/2009 | Baginski |
| 2011/0171736 | A1 | 7/2011 | Agnew et al. |
| 2012/0107942 | A1 | 5/2012 | Baginski |
| 2012/0165370 | A1 | 6/2012 | Tang et al. |

FOREIGN PATENT DOCUMENTS

| | | |
|---|---|---|
| CA | 2475011 | 7/2004 |
| EP | 0671401 | 9/1995 |
| EP | 0533200 | 12/2001 |
| EP | 1750126 | 12/2005 |
| EP | 1475632 | 5/2013 |
| JP | 10306075 | 11/1998 |
| JP | 11080107 | 3/1999 |
| JP | 2000510854 A | 8/2000 |
| WO | 03069328 | 8/2003 |
| WO | 2004027388 | 4/2004 |
| WO | 2005116629 | 12/2005 |
| WO | 2007069591 | 6/2007 |
| WO | 2009070233 | 6/2009 |
| WO | 2009100155 | 8/2009 |
| WO | 2011/146594 A2 | 11/2011 |

OTHER PUBLICATIONS

Jean-Michel Chezal, et al. "Evaluation of Radiolabeled (Hetero)Aromatic Analogues of N-(2-diethylaminoethyl)-4-iodobenzamide for Imaging and Targeted Radionuclide Therapy of Melanoma" J. Med. Chem. 2008, 51, 3133-3144.*
Liu, Hongji, et.al.; "Homogeneous Fluorescent Derivatization of Large Proteins"; Journal of Chromatography A, 927 (2001) pp. 77-89.
Ullmer, Roman, et.al.; "Derivatization by 6-aminoquinolyl-N-hydroxysuccinimidyl Carbamate for Enhancing the Ionization Yield of Small Peptides and Glycopeptides in Matrix-Assisted Laser Desorption/Ionization and Electrospray Ionization Mass Spectrometry"; Rapid Communications in Mass Spectrometry (2006) pp. 1469-1479.
Kinzel, Olaf, et al.; "Identification of MK-5710 ((8aS)-8a-methyl-1,3-dioxo-2[(1S,2R)-2-phenylcyclopropyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, Part 2"; Bioorganic & Medicinal Chemistry Letters; vol. 21 (2011) pp. 4429-4435.
European Search Report and Written Opinion dated Aug. 26, 2014 regarding patent application No. EP 12836127.6, 5 pages.
European Search Report and Written Opinion dated Feb. 2, 2016 regarding patent application No. EP 15180680.9, 7 pages.
Notice of Rejection, JP Application No. 2014-533416, dated Jan. 10, 2017. Original.
Notice of Rejection, JP Application No. 2014-533416, dated Jan. 10, 2017. Translated.
EP Communication pursuant to Article 94(3) EPC, EP Application No. 12836127.6, dated Sep. 26, 2016.
Decision on Rejection, Chinese Application No. 201280047599.3, dated Dec. 5, 2016, Translated.

(Continued)

*Primary Examiner* — Lyle Alexander
*Assistant Examiner* — Emily Berkeley
(74) *Attorney, Agent, or Firm* — Nielsen IP Law LLC (57) ABSTRACT

Mass spectrometry (MS) active, fluorescent rapid tagging reagent is provided having three substituent groups: (a) a tertiary amino group or other MS active atom; (b) a highly fluorescent moiety; and (c) a reactive group that can react with an amine. The reactive group provides rapid tagging of desired bio-molecules. The fluorescent moiety provides the fluorescent signal. The tertiary amino group provides the MS signal.

12 Claims, 2 Drawing Sheets

(56) References Cited

OTHER PUBLICATIONS

Decision on Rejection, Chinese Application No. 201280047599.3, dated Dec. 5, 2016, Original.
Restriction Requirement, U.S. Appl. No. 14/342,131, dated Aug. 17, 2016.
Non-Final Office Action, U.S. Appl. No. 14/342,131, dated Nov. 4, 2016.
Response to Restriction Requirement, U.S. Appl. No. 14/342,131, Sep. 28, 2016.
Response to Non-Final Office Action, U.S. Appl. No. 14/342,131, dated Feb. 6, 2017.
EP Communication with extended search report, EP Application No. 15180680.9, dated Feb. 2, 2016.
Response to EP Communication, EP Application No. 15180680.9, dated Sep. 2, 2016.
Hossler et al., Optimal and Consistent Protein Glycosylation in Mammalian Cell Culture, Glycobiology 2009; 19:936-49.
Anumula et al., High Resolution and High Sensitivity Methods for Oligosaccharide Mapping and Characterization by Normal Phase High Performance Liquid Chromatography Following Derivatization with Highly Fluorescent Anthranilic Acid, Glycobiology 1998; 8:685-94.
Marino et al., A Systematic Approach to Protein Glycosylation Analysis: A Path Through the Maze, Nature Chemical Biology 2010; 6:713-23.
Suzuki et al., Comparison of the Sensitivities of Various Derivatives of Oligosaccharides in LC/MS with Fast Atom Bombardment and Electrospray Ionization Interfaces, Anal Chem 1996; 68:2073-83.
Harvey, Identification of Protein-Bound Carbohydrates by Mass Spectrometry, Proteomics 2001; 1:311-28.
Yu et al., A Rapid Sample Preparation Method for Mass Spectrometric Characterization of N-linked Glycans, Rapid Comm Mass Spectrometry 2005; 19:331-36.
Klapoetke et al., The Evaluation of a Novel Approach for the Profiling and Identification of N-linked Glycans With a Procainamide Tag by HPLC With Fluorescent and Mass Spectrometric Detection, J. Pharmaceutical and Biomedical Anal 2010; 53:315-24.
Nimura et al., Activated Carbamate Reagent as Derivatizing Agent for Amino Compounds in High-Performance Liquid Chromatography, Anal Chem 1986; 58:2372-75.
Takeda et al., Convenient Methods for Syntheses of Active Carbamates, Ureas and Nitrosoureas Using N,N'-Disuccinimido Carbonate (DSC), Tetrahedron Lett 1983; 24:4569-72.
Wada et al., Comparison of the Methods for Profiling Glycoprotein Glycans—HUPO Human Disease Glycomics/Proteome Initiative Multi-Institutional Study, Glycobiology 2007; 17:411-22.
Wuhrer et al., Nano-Scale Liquid Chromatography-Mass Spectrometry of 2-Aminobenzamide-Labeled Oligosaccharides at Low Femtomole Sensitivity, Int J Mass Spectrom 2004; 232:51-57.
Heinze-Krauss et al., Structure-Based Design of β-Lactamase Inhibitors. 1. Synthesis and Evaluation of Bridged Monobactams, J Med Chem 1998; 41:3961-71.
Isbell et al., Effect of pH in the Mutarotation and Hydrolysis of Glycosylamines, JACS 1950; 72:1043-4.
Tarentino et al., 2-Iminothiolane: A Reagent for the Introduction of Sylphydryl Groups into Oligosaccharides Derived from Asparagine-Linked Glycans, Glycobiology 1993; 3:279-85.
Saurina et al., Chromatographic Determination of Amino Acids by Pre-Column Derivatization Using 1,2-Napthoquinone-4-Sulfonate As Reagent, J Chromatogr A 1996; 740:21-30.
Pieppenen et al., Rapid and Sensitive Step Gradient Assays of Glutamate, Glycine, Taurine and γ-Aminobutyric Acid by High-Performance Liquid Chromatography-Fluorescence Detection with o-Phthalaldehyde-Mercaptoethanol Derivatization With an Emphasis on Microdialysis Samples, J Chromatogr B 2001; 757:277-83.
Black et al., Simple, Rapid, and Highly Efficient Separation of Amino Acid Phenylthiohydantoins by Reversed-Phase High-Performance Liquid Chromatography, Anal Biochem 1982; 121:281-85.
Casoli et al., Use of High-Performance Liquid Chromatography for the Determination of Amino Acids in Sparkling Wines, Am J Enol Vitic 1982; 33:135-39.
Liu et al., Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis, J Chromatogr A 1998; 828:383-95.
Park et al., Regioselective Covalent Modification of Hemoglobin in Search of Antisickling Agents, J Med Chem 2003; 46:936-53.
Saurina et al., Determination of Amino Acids by Ion-Pair Liquid Chromatography With Post-Column Derivatization Using 1,2-Naphthoquinone-4-Sulfonate, J Chromatogr A 1994; 676:311-19.
Schmidt et al., Amino Acid Profiling of Protein Hydrolysates Using Liquid Chromatography and Fluorescence Detection, J Liq Chromatogr 1979; 2:1031-45.
Van Wandelen et al., Using Quaternary High-Performance Liquid Chromatography Eluent Systems for Separating 6-Aminoquinolyl-N-Hydroxysuccinimidyl Carbamate-Derivatized Amino Acid Mixtures, J Chromatogr A 1997; 763:11-22.
Wei et al., Study on N-Hydroxyphthalimide as Blocking Agent for Isocyanates, J Appl Polym Sci 2002; 84:1346-52.
Kurita et al., Synthesis and Properties of Polyurethanes Derived from bis-N-Hydroxyimides and Diisocyanates, J Polym Sci 1979; 17:1619-29.
Search Report and Written Opinion, PCT/US2012/057996 dated Jan. 31, 2013.
Vasilevich et al., Conversion of O-Succinimidyl Carbamates to N-(O-Carbamoyl)-Succinmonoamides and Ureas: Effects of N-Substituents and Reaction Conditions on the Reaction Pathway, Tetrahedron Lett 2002; 43:6649-52.
Guichard et al,. Preparation of O-Succinimidyl-2-(tert-Butoxycarbonylamino)ethylcarbamate Derivatives from Beta-Amino Acids. Application to the Synthesis of Urea-Containing Pseudopeptides and Oligoureas, J Org Chem 1999; 64:8702-5.
Cooper et al., LC-MS/MS Analysis of AccQ-Tag Derivatised Amino Acids, Micromass Application Brief, Sep. 200 and Jun. 2000.
Cohen, Compositional Protein Analysis Using 6-Aminoquinolyl-N-Hydroxysuccinimidyl Carbamate, a Novel Derivatization Reagent, Techniques in Prot Chem IV 1993; 289-298.
De Antonis et al., High-Performance Liquid Chromatographic Analysis of Synthetic Peptides Using Derivatization with 6-Aminoquinolyl-N-Hydroxysuccinimidyl Carbamate, Anal Biochem 1994; 223:191-7.
Liu et al., Femtomole Peptide Mapping by Derivatization, High-Performance Liquid Chromatography, and Fluorescence Detection, Anal Biochem 2001; 294:7-18.
Cohen et al., Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography, Anal Biochem 1993; 211:279-87.
Higashi et al., Derivatization of Neutral Steroids to Enhance Their Detection Characteristics in Liquid Chromatography-Mass Spectrometry, Anal Bioanal Chem 2004; 378:875-882.
Hochleitner et al., Determination of the Stoichiometry of Protein Complexes Using Liquid Chromatography with Fluorescence and Mass Spectrometric Detection of Fluorescently Labeled Proteolytic Peptides, Proteomics 2004; 4:669-676.
Schmeer et al., Compositional Analysis of the Phenylthiocarbamyl Amino Acids by Liquid Chromatography-Atmospheric Pressure Ionization Mass Spectrometry with Particular Attention to the Cyst(e)ine Derivatives, J of Chromatography 1995; 691:285-99.
Martinez-Force et al., Separation of O-Phthalaldehyde Derivatives of Amino Acids of the Internal Pool of Yeast by Reverse-Phase Liquid Chromatography, Biotech Tech 1991; 5(3):209-14.
Block, The Use of 6-Aminoquinolyl-N-Hydroxy Succinimidyl Carbamate Derivatives for HPLC/MS Analysis of Amino Acids, AMD35 Waters Alliance LC/MS System 2000.

(56) References Cited

OTHER PUBLICATIONS

Cooper et al., LC-MS/MS Analysis of AccQ-Tag Derivatised Amino Acids, Micromass UK Limited 2000.
Block et al., Abstract 2050P: HPLC-MS Analysis of Amino Acids, Pittsburgh Conference, Mar. 1999.
Block et al., Poster 2050P: HPLC/MS Analysis of Amino Acids: The Use of 6-Aminoquinolyl-N-Hydroxy-Succinimidyl Carbamate Derivatives, Pittsburgh Conference, Mar. 1999.
Cooper et al., LC-MS-MS Analysis of Amino Acids Using AccQ-Tag derivatisation, Application Brief AB25, Micromass Jun. and Sep. 2000.
Block, Presentation: LC/MS Application Notes: The Use of 6-Aminoquinolyl N Hydroxy Succinimidyl Carbamate Derivatives for HPLC/MS Analysis of Amino Acids, Pittsburgh Conference, Mar. 1999.
Chromatography Forum: LC-MS & GC-MS Archives: AAA LC-MS, http://www.lcresources.com/discus/messages/5135/3143.html?MondayApril1420030826pm Jan.-Apr. 2003.
EP Communication under Rule 71(3) EPC, EP Application No. 12836127.6, dated Mar. 15, 2017.
Mazzocchi, Paul H. et al., "A Photochemical Route to Pyrrolo[1,4]Benzodiazepine Antitumor Antibiotics" Heterocycles 1985, 1603-1606, vol. 23, No. 7.
Holmes, Darren L. et al., "Solid-Phase Synthesis of Artificial beta-Sheets" J. Am. Chem. Soc. 1997, 119, 7665-7669.
International Search Report and Written Opinion, Apr. 27, 2017, PCT/US 2017/014790, 7 pages.

\* cited by examiner

RAPID FLUORESCENCE TAGGING OF GLYCANS AND OTHER BIOMOLECULES WITH ENHANCED MS SIGNALS

CROSS REFERENCE TO RELATED APPLICATIONS

This application is a continuation of International Application No. PCT/US12/57996 filed Sep. 28, 2012, which claims the benefit under 35 U.S.C. §119 (e) of U.S. Provisional Application No. 61/540,306 filed Sep. 28, 2011.

STATEMENT REGARDING FEDERALLY SPONSORED RESEARCH OR DEVELOPMENT

None.

THE NAMES OF PARTIES TO A JOINT RESEARCH AGREEMENT

None.

INCORPORATION-BY-REFERENCE OF MATERIAL SUBMITTED ON COMPACT DISC

None.

BACKGROUND OF THE INVENTION

Fluorescent labeling of N-glycans is beneficial to detecting glycans because it improves both sensitivity and selectivity of the detection as well as the chromatographic behavior of glycans. Amino acid analysis is a fundamental process in protein research and is of particular importance to clinical chemists and pharmaceutical manufacturers when glycosylation profiling of proteins must be monitored to ensure consistency of a therapeutic product. Upon derivation with a reagent having a fluorescent moiety, the functional group of the compound can only be estimated. Mass spectrometry ("MS") is then required to identify the specific compound.

Analysis by MS has reached a high degree of development with respect to glycan and amino acid analysis and proteomics. However, the necessary reaction time to functionalize most amines is slow. The current state of the art utilizes tagging molecules that either (1) react quickly and have good fluorescence signal, but poor MS signal or (2) react very slowly and give good MS/fluorescence signals. A combination of MS and fluorescence detection is desirable, however, because fluorescence detection is very useful tool in determining quantitatively how much is present. On the other hand, MS is used to determine what the molecular makeup is.

A need exists, therefore, for molecules with that rapidly react with biomolecules and provide strong mass spectrometry and fluorescence signals.

SUMMARY OF THE INVENTION

Described herein are MS active molecules useful for rapid fluorescence tagging of glycans such as N-linked glycans and other bio-molecules such as proteins and peptides and amino acids. These MS active, fluorescent molecules can have three functional components: (a) a tertiary amino group or other MS active atom; (b) a highly fluorescent moiety, and (c) a functional group that rapidly reacts with amines, such as an isocynanate or succidimidylcarbamate. The reactive functional group provides rapid tagging of desired biomolecules, and the fluorescent moiety provides for a strong fluorescent signal. The tertiary amino group substituent provides a strong MS signal. In another aspect, presented herein are rapid tagging MS active compounds which do not have a fluorescent moiety.

In particular, the invention relates to compounds of Formula I and Formula II as shown immediately below, and uses of the same in rapid fluorescence tagging of glycans having enhanced MS signals.

Formula I wherein
$R^1$ is O=C=N— or

;

$R^2$ is independently selected from —H, —$C_1$-$C_8$ alkyl, —$C_1$-$C_8$ cycloalkyl, halo, dialkylamino, $CH_2$-dialkylamino, aminocarbonyl, alkoxycarbonyl, or alkoxy, but not Cl or O=C=N—; and $R^3$ and $R^4$ are independently selected from —H, alkyl, alkyl amino, alkylsulfonic acid, alkyl phosphonic acid, wherein $R^3$ or $R^4$ is alkylamino, alkyl phosphonic acid, or alkylsulfonic acid, and wherein $R^3$ and $R^4$ together with the nitrogen to which they are attached may form an optionally substituted 5- to 8-membered saturated or partially unsaturated ring but not when $R^1$ is O=C=N—.

Formula II wherein
m=0-9;
n=0-9;
$R^1$ is O=C=N—, S=C=N—, or

;

$R^2$ is independently selected from methylene, substituted nitrogen, oxygen, carbonyl, amide, ester, sulfur, sulfoxide, or sulfone;

$R^3$ and $R^4$ are independently selected from —H, alkyl, alkyl amino, alkylsulfonic acid, alkyl phosphonic acid, wherein $R^3$ or $R^4$ is alkylamino, alkyl phosphonic acid, or alkylsulfonic acid, and wherein $R^3$ and $R^4$ together with the nitrogen to which they are attached may form an optionally substituted 5- to 8-membered saturated or partially unsaturated ring; and $R^5$ is independently selected from —H, —$C_1$-$C_8$ alkyl, —$C_1$-$C_8$ cycloalkyl, halo, dialkylamino, $CH_2$-dialkylamino, aminocarbonyl, alkoxycarbonyl, or alkoxy, but not Cl or O=C=N—, and not when $R^1$ is S=C=N.

The compounds of Formula I and/or II may have optical centers and therefore may occur in different enantiomeric and diastereomeric configurations. The invention described herein includes all enantiomers, diastereomers and other stereoisomers of such compounds of the Formula I and of Formula II, as well as racemic compounds and racemic mixtures and other mixtures of stereoisomers thereof.

DETAILED DESCRIPTION

Novel compounds of Formula I and Formula II as presented herein are useful in the rapid fluorescence tagging of glycans and amino acids with enhanced signals. The compounds are useful for analyzing glycans and can be used to analyze proteins and amino acids in a sample containing at least one of the same. To analyze a molecule, the molecule is rapidly labeled with the compounds described herein and subjected to liquid chromatography, mass spectrometry, and fluorescence detection.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds presented herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position The development and production of therapeutic proteins is becoming the fastest-growing segment of the pharmaceutical industry. The efficacy, stability and protein secretion of these large molecule drugs depend on their Post Translational Modifications ("PTMs"). Glycosylation is the most complex and common PTM and plays a vital role in the safety and efficacy of many therapeutic proteins such as recombinant antibodies. Several studies have shown the correlation between glycosylation variations caused by cell line selection and changes in culture medium parameters. Patrick Hossler et al., *Optimal and Consistent Protein Glycosylation in Mammalian Cell Culture*, 19 GLYCOBIOLOGY 926 (2009). These variations can have a profound effect on the biological activities of the mAb drugs, which leads to changes in drug potency in the final product. Regulatory agencies require monitoring of batch-to-batch recombinant antibody drug production quality and mandate detailed assessment of the protein glycosylation micro-heterogeneity and consistency.

Other novel compounds of Formula I and Formula II which are useful in the rapid fluorescence tagging of glycans and amino acids with enhanced signals are shown below.

2,5-dioxopyrrolidin-1-yl (4-((2-(diethylamino)ethyl)carbamoyl)phenyl)carbamate and Further additional compounds useful in the rapid fluorescence tagging of glycans and amino acids with enhanced signals are shown immediately below.

Also provided herein is a method for analyzing a glycan, an amino acid or a protein in a sample containing at least one glycan by means of liquid chromatography and mass spectrometry comprising labeling the glycan in the sample by reacting the glycan with a compound according to Formula III for a time and under conditions suitable to facilitate the labeling; providing a sample containing the glycan labeled with the compound; and subjecting the labeled compound to liquid chromatograph and mass spectrometry wherein the compound of Formula III is:

wherein
x=0 or 1;
m=0-9;
n=0-9;
Ar is selected from optionally substituted phenyl group, naphthyl group, anthryl group, pyridyl group, pyrazyl group, quinolyl group, acridly group, and coumaryl group, and in combination with a carbonyl group produces a fluorescent moiety;
$R^2$ is a reactive group selected from the group consisting of N-succinimidyl carbamate, isocyanate, and isothiocyanate;
$R^3$ and $R^4$ are independently selected from the group consisting of —H, alkyl, alkyl amino, alkylsulfonic acid, and alkyl phosphonic acid, lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea, wherein two substituents can be joined together to form a fused five-, six-, or seven-membered carbocyclic or heterocyclic ring consisting of zero to three heteroatoms and the optionally substituted group can be unsubstituted, fully substituted, monosubstituted or substituted at a level anywhere in-between fully substituted and monosubstituted and $R^3$ and $R^4$, alone or in combination, can be MS active;
$R^5$ is lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea, wherein two substituents can be joined together to form a fused five-, six-, or seven-membered carbocyclic or heterocyclic ring consisting of zero to three heteroatoms, wherein the optionally substituted group can be unsubstituted, fully substituted, monosubstituted or substituted at a level anywhere in-between fully substituted and monosubstituted, and $R^5$ can be MS active, but when $R^5$ is MS active, $R^3$ and $R^4$ are H; and
$R^6$ is independently selected from methylene, substituted nitrogen, oxygen, carbonyl, amide, ester, sulfur, sulfoxide, or sulfone and can be MS active.

N-linked and O-linked glycans are common glycans from recombinant biotherapeutic proteins, N-glycans being the more prominent. N-linked glycans are attached to asparagines via an N-acetylglucosamine ("GlcNAc") residue in an Asn-Xxx-(Ser, Thr) motif where Xxx can be any amino acid except proline. O-linked glycans are attached to either Serine or Threnine. N-linked glycans can be removed from the glycoprotein chemically or enzymatically. Analytical methods of analyzing N-linked glycans have become considerably sophisticated. CE-, HPAEC-PAD, HILIC-LC/FLR, RPLC/MS, MALDI-MS are the most common analytical instrumentations. Liquid chromatography ("LC") separation with fluorescence detection is widely used in the pharmaceutical industry for the characterization of enzymatically/chemically released glycan, typically tagged with a fluorescent dye at the reducing end of a glycan. Kalyan R. Anumula & Shirish T. Dhume, *High Resolution and High Sensitivity Methods for Oligosaccharide Mapping and Characterization by Normal Phase High Performance Liquid Chromatography Following Derivatization with Highly Fluorescent Anthranilic Acid,* 8 GLYCOBIOLOGY 685 (1998); Karina Mariño et al., *A Systematic Approach to Protein Glycosylation Analysis: A Path Through the Maze,* 6 NATURE CHEMICAL BIOLOGY 713 (2010). Fluorescent measurements are sensitive and quantitative; the low detection limit is in the low femtomoles. With recent advancements in mass spectrometry instrumentation, the combination of liquid chromatography, fluorescence and MS has gained more popularity as an analytical instrument platform for routine characterization of fluorescently labeled N-linked glycans. Therefore, relative quantitation and molecular weight measurements can be done in a single analysis. Shigeo Suzuki et al., *Comparison of the Sensitivities of Various Derivatives of Oligosaccharides in LC/MS with Fast Atom Bombardment and Electrospray Ionization Interfaces*, 1006 ANAL CHEM 2073 (1996). However, another challenge is that glycans do not ionize efficiently via electro-spray-ionization ("ESI"). Therefore, in general, tagging with an MS active moiety is required.

The sample preparation step can be very time consuming as it requires enzymatic digestion on the protein to release N-linked glycans followed by fluorescence tagging reaction. For example, the derivatization with a fluorescence moiety accomplished by reductive amination can require up to 4 hours. Derivatization using the aromatic amine, 2-aminobenzamide (2AB), is the most established method and requires this reductive amination. The 2AB tag improves the MS sensitivity compared to the non-labeled glycan and is fluorescently active.

Provided herein is a rapid method for fluorescent tagging N-linked glycans using novel chemical reagents. These tags are designed to enhance the analyte mass spectrometry response. This same chemical tag may be used for amino acid and peptide labeling. The reaction mechanism may be the same for all three types of molecules, whereby the derivatization occurs at the amine moiety. Amino acid analysis, peptide mapping and glycan profiling are each an integral part of the overall biotherapeutic protein characterization. Therefore, it is advantageous to have rapid universal fluorescent derivatization methods which improve detection of the MS instrumentation.

New molecules (also referred herein to as "reagents") specific for N-linked glycans amino acids and peptides, are provided for enhanced MS detection and rapid fluorescence tagging of glycans and other biomolecules with enhanced MS signals. Through the use of these reagents, the reaction times necessary to carry out the tagging process (or otherwise sometimes referred to herein as "labeling") is measured in seconds, rather than minutes or hours. The described molecules are useful in a wide variety of processes that rely on glycan and amino acid/peptide analysis for essential information of a product, process, or protein. As such, the molecules described herein may be used in processes such as protein characterization, cell culture monitoring, synthetic peptide manufacturing, and food analysis.

The reagents provided herein can consist of three functional components a) a tertiary amino group or other MS active atom, b) a highly fluorescent moiety, and c) a functional group that rapidly reacts with amines (such as an isocyanate, or succidimidylcarbamate). Other reagents can consist of two functional components a) a tertiary amino group or other MS active atom, and b) a functional group that rapidly reacts with amines (such as an isocyanate, or succidimidylcarbamate). The components serve the following purposes: (1) the amino group or MS active group gives good MS signal; (2) the fluorescent moiety provides a good fluorescence signal; and (3) the reactive functional group gives rapid tagging of desired biomolecules.

The enhanced MS signal observed upon utilization of a 2AB tagging reagent (slow reaction-hours), for example, is a function of the amino or amine group present in the system following tagging. Currently available rapid tagging agents contain no amino functionality following tagging of the desired biomolecule. Rather, these compounds have functionalities which do not provide the same electron density for mass spectrometry applications (e.g., urea or carbamate) and tie up the electron density resulting in low MS signal.

Biomolecules are organic compounds that are involved in the maintenance and metabolic processes of living organisms. Many disease conditions are due to impaired amino acid metabolism (e.g. phenylketonuria). As noted above, a biomolecule can also be a therapeutic agent such as peptide based pharmaceuticals that have been used to treat the disease. Glycans, amino acids, peptides and proteins are closely monitored during protein drug development and production. Many biomolecules can be detected by tagging them with a fluorescent label. The resulting conjugate or complex will show fluorescence, thereby facilitating their detection. There is recent movement in the industry towards using MS for detection and quantitation of biomolecules. Fluorescent detection is still widely used for its sensitivity and quantitative analysis. Therefore, the combination of liquid chromatography, mass spectrometry and fluorescent detection is an analytical platform that can be used for a comprehensive protein analysis. Notwithstanding, there is no single technique that is capable of providing a complete structural analysis of N-linked glycans.

Mammalian and plant glycoproteins are biomolecules that commonly contain any one or more three types of constituent glycans, oligo- and polysaccharides. Glycans are important for protein folding and any alteration thereof may eliminate or alter activity. Often an immune response is triggered by an unrecognized glycan. Of the three types of glycans, analytical methods of analyzing N-linked glycans have become considerably sophisticated.

Structurally, N-linked glycans are attached to asparagines via an N-acetylglucosamine (GlcNAc) residue in an Asn-Xxx-(Ser, Thr) motif where Xxx can be any amino acid except proline. The N-glycan can be removed from the glycoprotein with hydrazine whether manually or with the aid of automated hydrazinolysis equipment. The reagent cleaves peptide bonds between the N-linked glycan and asparagines to produce the glycan biomolecule. Several enzymes are available for releasing N-glycans. N-glycosidase F (PNGase-F), a commonly used enzyme, cleaves the intact glycan as the glycosylamine leaving aspartic acid in place of the asparagine at the N-linked site of the protein. Harvey, D. J., *Identification of Protein-Bound Carbohydrates by Mass Spectrometry*, 1 PROTEOMICS 311 at 311-312, 317 (2001), incorporated herein by reference.

Detection of Molecules by MS and Fluorescence

Most amino acids and/or glycans are not readily detectable due to the absence of a strong chromophore or fluorophore or MS active moiety. The absorbance and fluorescence response are quite weak. A commonly used tactic to maximize the sensitivity of an assay is to convert the compound of interest into a derivative that exhibits a better response for the particular detection method being utilized. The selection of a derivatizing agent is a critical choice in the development of an analytical procedure. The derivatizing agent affects the ultimate sensitivity and accuracy of the analysis by maximizing the sensitivity, yield and stability of the derivatized molecules.

Basically, the following determinations must be performed separately: (1) the glycosylated sites; (2) the glycosylated site occupancy; (3) the structure and amount of each glycan at each site: and (4) the number of glycoforms. Id. at 312, incorporated herein by reference. In most situations, MS can provide the answers to each of these steps. Hence the need for enhanced MS signals. Because of the branched nature of the glycan, however, structural determination of the glycan is complicated. Here, the monosaccharide unit, the anomericity and ring size of each monosaccharide, the monosaccharide sequence and ring conformation together with identification of other groups must be determined. With the exception of ring conformation, MS can be used directly or indirectly to make these determinations using MALDI and/or ESI as the preferred MS technique. Id. at 313-316, incorporated herein by reference.

Currently, for N-glycans, derivatives are most commonly added to the reducing terminus of the glycan by reductive amination reaction with an aromatic amine. Id. at 318-319. Reducing-Terminal Derivatization, incorporated herein by reference. Reductive amination, while producing an MS active compound, is a very slow process and can take four (4) hours to tag the reagent to the compound. Reducing-terminal derivatives may also be prepared by reactions other than reductive amination. Id. at 319, incorporated herein by reference.

Most glycans are not readily detectable due to the absence of a strong chromophore or fluorophore. Free glycans released from glycoproteins enzymatically or chemically can be analyzed directly via MALDI MS or ESI/MS/MS directly without any chemical tagging. Ying Qing Yu et al., *A Rapid Sample Preparation Method for Mass Spectrometric Characterization of N-linked Glycans*, 19 RAPID COMM. MASS SPECTROMETRY 2331 (2005). This label-free approach is suitable for qualitative analysis for glycans. However, this approach is not as well suited for relative quantitation due to the fact that glycans from a single protein sample can be very heterogeneous in that the ionization efficiency is not the same among them. Therefore, a single analysis platform that can perform both quantitative and qualitative analysis is desirable. Since a fluorescent detector only detects the dye itself, the fluorescent response from various glycans can be used for relative quantitation. The selection of a derivatizing agent is a critical choice in the development of an analytical procedure. For N-glycans, derivatives are often added to the reducing terminus of the glycan by reductive amination reaction with an aromatic amine. Reductive amination, while producing an MS active compound, is a very slow process and can take up to four hours to complete. There are many aromatic amine compounds that are used for reductive amination for glycans, most of them giving a low to moderate MS response. Recently, it was reported that procainamide can be used to enhance glycan MS response. Song Klapoetke et al., *The Evaluation of a Novel Approach for the Profiling and Identification of N-linked Glycans With a Procainamide Tag by HPLC With Fluorescent and Mass Spectrometric Detection*, 53 J. PHARMACEUTICAL AND BIOMEDICAL ANAL. 315 (2010). A significant increase of glycan ionization was observed when compared with 2AB-labeled glycans. Id. However, procainamide labeling procedure is similar to other commonly used reductive amination reagents, and therefore, it still takes a half day for the labeling step.

As such, fluorogenic derivatization prior to an HPLC analysis of amino acids currently serves as an efficient tool in the analysis of these systems. For example, phanquinones and benzooxadiazoles are nitrogen containing fluorophores that can be used as pre-column derivatization agents. These compounds are devoid of intrinsic fluorescence. However, on conjugation with amino acids, they form the corresponding fluorescent conjugates.

Uses of the Reagents Presented

The present molecules can be particularly useful for derivatizing glycans and also amino acids and proteins because they react quickly with the molecules and form a stable, highly fluorescent MS derivative. The general methodology for an analysis of a glycan or amino acid using the compounds of the subject invention consists of three closely related processes: (1) formation of derivatives in the sample; (2) separation of the derivatives; and (3) detection of the separated derivatives. The first step is generally performed by reacting a mixture with one of the present reagents to yield a distinct compound. These derivatives provide a fluorescent signal which can then be detected in the detection stage of the analysis.

The separation step is based upon the differences in the chemical structure of the derivatives. The derivatized amino acids differ from each other in the same way that the chemical structures of the precursor amino acids differ. The derivatives must be separated so that the detector signal can be correctly related to the concentration of each derivative. The derivatized amino acids can be separated and detected by chromatography, e.g., by high performance liquid chromatography (HPLC) or capillary zone electrophoresis (CZE). HPLC is particularly useful for this purpose. These technologies are well suited for this purpose because they are selective and can be used with very small samples. It is also possible to carry out the separation step by separating the amino acids prior to their derivatization.

The detection step is generally carried out using either an absorbance or fluorescence detector. As each derivative is eluted from the chromatographic column after separation, its presence and quantity is detected by a mass spectrometer and/or by the absorbance or emission of light. The sensitivity of the assay depends upon the strength of the signal produced.

In the case of peptide analysis, reverse phase HPLC can be also used to analyze the peptide digests. In a given peptide digest there may be from 20 to 150 different peptides, each of which must be resolved and quantified. In many instances, the available sample is very small. For example, the analyst may be determining the structure of a protein that is isolated from an organism or one that has been synthesized by recombinant DNA technologies. Typically, nanomole quantities of a protein digest are studied. Due to the scarcity and cost of many proteins, it is very desirable to use as small a sample as possible.

Figure 1:
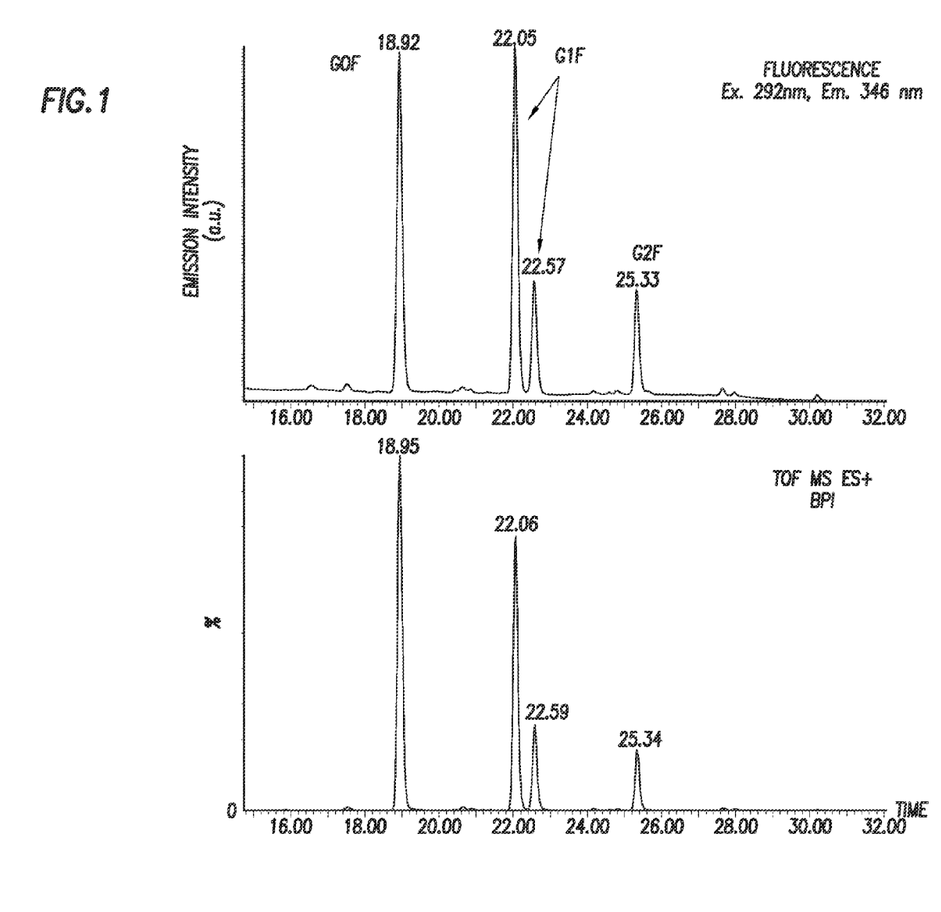
FIG. 1 shows the fluorescence and MS detection of the glycans G0F, G1F, and G2F released from 0.8 µg Herceptin IgG labeled with 2,5-dioxopyrrolidin-1-yl (4-((2-(diethylamino)ethyl)carbamoyl)phenyl)carbamate.
Figure 2:
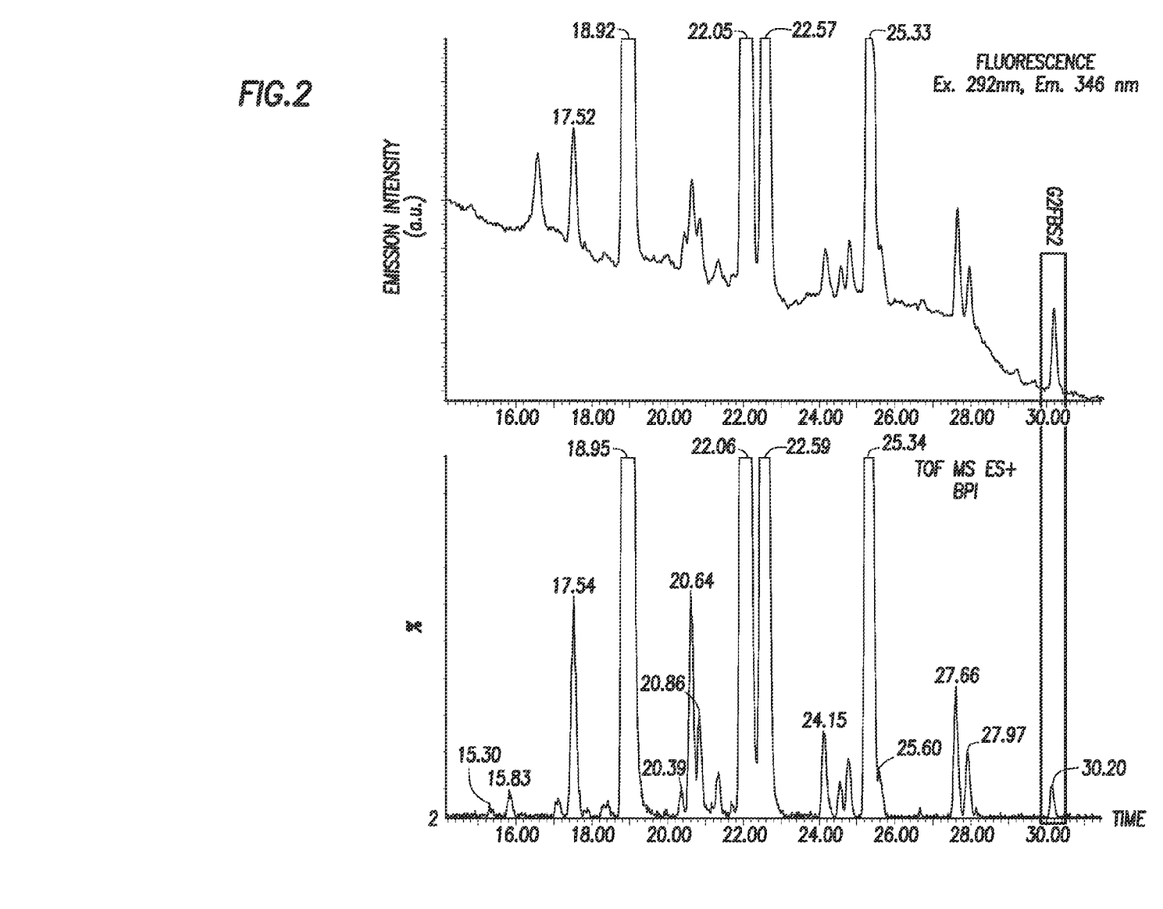
FIG. 2 shows the fluorescence and MS detection of the glycan G2FBS2 released from 0.8 µg Herceptin IgG labeled with 2,5-dioxopyrrolidin-1-yl (4-((2-(diethylamino)ethyl)carbamoyl)phenyl)carbamate.

As described in Example I below, we tested the labeling of N-linked glycans with 2,5-dioxopyrrolidin-1-yl (4-((2-(diethylamino)ethyl)carbamoyl)phenyl)carbamate. Here, N-linked glycans were released from a glycoprotein (Herceptin) using PNGase F prior to labeling with 2,5-dioxopyrrolidin-1-yl (4-((2-(diethylamino)ethyl)carbamoyl)phenyl) carbamate. The 2,5-dioxopyrrolidin-1-yl (4-((2-(diethylamino)ethyl)carbamoyl)phenyl)carbamate was solubilized in water free acetonitrile to a final concentration of 45 µg/µl. 100 µl of 2,5-dioxopyrrolidin-1-yl (4-((2-(diethylamino)ethyl)carbamoyl)phenyl)carbamate solution was added to the released glycan sample and left at room temperature for 5 minutes, during which time the labeling reaction finished. The labeled sample was lyophilized using a speed vac. The lyophilized sample was reconstituted in 60% acetonitrile/water solution prior to chromatographic separation using HILIC LC method. As shown in FIGS. 1 and 2, the samples were analyzed using fluorescence and MS detection.

Additional Uses for the Molecules Presented Herein

Absorbance detection is generally used in protein mapping work. Two different detection processes which are often used for this purpose are: a) detection at 210-215 nm using a single wavelength detector; and b) broadband spectral detection using a photodiode array (PDA) detector. In the first method, all peptides absorb at that wavelength, thus the user can ensure that all peptides eluted from the column are detected. One difficulty with this technique is that a wide variety of compounds absorb in this region of the spectrum, and extreme care must be taken to ensure that all reagents, eluents, glassware, etc. are scrupulously clean to ensure that the observed signal is solely from the peptides. In the second method, the PDA detector collects the spectra of the eluent at specific time intervals (e.g. a spectrum between 200 and 350 nm is collected every second). This provides more information than a single wavelength and thus can assist in distinguishing between peptides which may elute with similar retention times.

Peptide mapping often involves the qualitative and quantitative analysis of trace levels of peptides in the digested protein. The identification and quantitation of peptides in complex mixtures in the present method is effected by a three stage process: a) tagging the peptides of interest with the heterocyclic aromatic carbamates or other reactive groups, which exhibit a stronger absorbance or fluorescence signal than the original compound; b) separating the derivatized samples; and c) detecting the derivatized peptides by absorbance or fluorescence techniques. The separation conditions for a derivative are frequently drastically different from the separation of the starting compounds. Likewise, the efficiency of a separation has a serious impact on the detection process. Use of the present heterocyclic aromatic carbamates and/or similar reactive groups provides a mapping method adaptable for use with nanogram quantities of protein. Further, the methods described herein provide a means for enhancing the sensitivity of known methodologies for detecting peptides in biological samples, such as tissue, urine, blood and saliva.

Derivatization Agent Selection

There are several criteria important for the utility of a derivatization method. The analytical procedure must provide accurate quantitation of each component present in a complex mixture. To accomplish this, it is necessary to resolve the components of interest, not only from each other, but from components generated by the derivatization procedure. Quantitative conversion of all underivatized glycans and amino acids, including secondary amino acids, to single products is highly desirable, and facilitates good quantitation.

Detection selectivity is another advantageous feature for amino acid derivatives. Underivatized amino acids all absorb weakly in the low UV (200-220 nm) range, but detection at such wavelengths is subject to interference by many compounds present in sample mixtures or chromatographic mobile phases. Derivatization with reagents absorbing at approximately 254 nm provides a measure of selectivity, but any aromatic organic compounds, frequently present in biological samples, can interfere at this wavelength. Reagents that enable detection via fluorescence, electrochemical response or visible-range absorbance would be desirable for superior detection selectivity.

Finally, it is necessary for derivatives to be sufficiently stable to allow separation and detection without significant degradation. Highly stable derivatives are also favorable as they allow a sample to be reanalyzed, if so desired, without assaying another sample.

In the past, a number of derivatization procedures have been developed to permit the assay of amino acids by high performance liquid chromatographic and electrophoretic separations. Five such procedures commonly utilized for this purpose include:

(1) The o-phthalaldehyde (OPA)/mercaptan method. The OPA procedure can detect amino acids with a typical detectable level in the order of about 100 femtomole (fmol). The formation of the derivatives is rapid. A significant difficulty with this method is the adduct is fairly unstable, and must be prepared very shortly before the detection step. An additional problem is that this reagent will not form a derivative with secondary amino acids.

(2) The 9-fluorenylmethylchloroformate (FMOC method). The FMOC procedure provides for stable derivatives, with a minimum detectable level in the order of a few hundred fmol. There are a number of disadvantages with the FMOC procedure. Free tryptophan and cystine cannot be quantitated easily. The derivatizing reagent must be removed from the reaction mixture by an extraction step because it is itself fluorescent. The reagent has also been reported to form multiple derivatives with histidine. The reagent is also hazardous to work with, because it is corrosive and is a lachrymator.

(3) The phenylisothiocyanate method (PITC). The PITC procedure yields stable derivatives which are formed rapidly. It can be used for both primary and secondary amino acids, as well as cystine. The method uses absorbance as the detection procedure, and can provide a minimum detection limit of 1 pmol. However, the derivatives are not fluorescent and detection must be performed at 254 nm, which does not allow for good detection selectivity.

(4) The dansyl chloride method. The dansyl chloride method provides stable derivatives with a minimum detectability in the order of about 1.5 pmol. It is able to detect secondary amines and cysteine, but it results in multiple derivatives.

(5) Fluorescent succinimidocarbamates have been used as derivatizing agents for amines, amino acids, peptides, phosphates and other classes of compounds. When the succinimidocarbamate reagent is used to tag a compound with a fluorescent group, a detection limit of about 1 pmol can be achieved. These reagents are used in conjunction with modern separation techniques such as high performance liquid chromatography, thin layer chromatography or capillary electrophoresis. Nimura et al., 58 ANAL. CHEM. 2372 (1986). Succinimidyl activated carbamates have been prepared by reacting carbocyclic aromatic amines with di-(N-succinimidyl) carbonate. Takeda et al., 24 TETRAHEDRON LETT., 4569 (1983).

Current derivatization chemistry for HPLC analysis of a broad range of samples includes Waters' AccQTag Amino Acid Analysis System. Waters AccQTag method is a pre-column derivatization technique for peptide and protein hydrolysate amino acids. The AccQTag methodology is based on a derivatizing reagent developed specifically for amino acid analysis. Waters AccQFluor reagent (6-aminoquinolyl-N-hydrozysuccinimidyl carbamate, or ACQ) is an N-hydroxysuccinimide-activated heterocyclic carbamate, a known class of amine-derivatizing compounds. See, EP0533200 B1.

This reagent converts both primary and secondary amino acids to stable, fluorescent derivatives and hydrolyzes to yield 6-aminoquinoline, a non-interfering byproduct. The AccQFluor reagent reacts rapidly with primary and secondary amino acids to yield highly stable ureas that fluoresce strongly at 395 nm. The resulting derivatives are stable at room temperature for up to one (1) week.

The key to the rapid and simple Waters AccQTag Amino Acid Analysis method is the derivatizing reagent and a simple, pre-column derivatization protocol. Waters AccQ-Fluor Reagent is a highly reactive compound, 6-aminoqui- nolyl-N-hydroxysuccinimidyl carbamate (AQC), which forms stable derivatives with primary and secondary amino acids in a matter of seconds. The derivatives are easily separated by reversed phase HPLC using Waters AccQTag Amino Acid Analysis System in less than 35 minutes.

Excess reagent is consumed during the reaction to form aminoquinoline (AMQ). AMQ has significantly different spectral properties than any of the derivatized amino acids. This allows for the programming of a detector wavelength that maximizes the spectral emission response of the derivatives while minimizing the response of the AMQ. The derivatization protocol—adding reagent to and heating a properly buffered sample—is simple and straight forward. The amino acid derivatives can be injected directly without further sample preparation. Common buffer salts and detergents have little effect on reaction yield or on the reproducibility of results.

Another example of derivatization chemistry for HPLC analysis of a broad range of samples is the InstantAB™ kit, a labeling kit used to produce tagged N-linked glycans and currently manufactured by Prozyme, for example, the Glyko® InstantAB™ kit (available from Prozyme, Inc., Hayward, Calif.) a sample preparation kit used to produce tagged N-linked glycans of the formula

InstantAB™, a compound of the formula provides rapid tagging and strong fluorescence but produces a weak MS signal. In fact, the MS signal of this molecule is significantly reduced when compared to the standard 2-AB reagent.

Presented herein are molecules that contain a tertiary amine, a fluorescent moiety and a reactive functional group. Certain other molecules may simply contain the tertiary amine and reactive functional groups. All molecules, however, undergo rapid functionalization. Through the use of a tertiary amine, all of the molecules are MS active (active in mass spectrometry), while others may also be fluorescent.

Below is a new molecule and reagent useful in mass spectrometry application and are fluorescent:

2,5-dioxopyrrolidin-1-yl (4-((2-(diethylamino)ethyl)carbamoyl)phenyl)carbamate

As noted above, the current state of the art utilizes tagging molecules that either 1) react very slowly and give good MS/fluorescence signals or 2) react quickly and have good fluorescence signal, but have poor MS signal. The lack of MS signal in the currently rapid reacting molecules is believed to arise from the lack of an electron rich amine—any nitrogen present loses electron density as part of urea or carbamate functionality. Herein, we provide the addition of an amino group or other MS active atom to the fluorescent moiety of the rapidly reacting systems, or alternatively, adding a reactive functional group to the slow reacting (high fluorescence and MS signal) system in order to decrease reactivity time (from hours to seconds).

Other fluorescent moieties may be useful in connection with the molecules described herein include coumarins, an important class of oxygen-containing fluorophores commonly used for labeling amino acids. Coumarins are a variety of substituted coumarins having a base molecular structure as follows:

A specific example is coumarin 7 (3-(2'-Benzimidazolyl)-7-N,N-diethylaminocoumarin) where the red R group (H on the parent coumarin) can be an isocyanate, an O-succinimidylcarbamate, or other amine reactive group.

Another example is a functionalized coumarin 334 (2,3,5,6-1H,4H-Tetrahydro-9-acetylquinolizino-[9,9a,1-gh]-coumarin) utilizing the carbonyl group as a functional handle to attach the reactive moiety.

Also, the following Nile Red derivative is functionalized through the phenol group to give an amine reactive group.

Nile Red Derivative

Other examples of coumarins useful as a fluorescent moiety include:
- Coumarin 4 (7-Hydroxy-4-methylcoumarin);
- Coumarin 120 (7-Amino-4-methylcoumarin);
- Coumarin 2 (7-Amino-4-methylcoumarin);
- Coumarin 466 (7-Diethylaminocoumarin);
- Coumarin 47 (7-Diethylamino-4-methylcoumarin);
- Coumarin 102 (2,3,5,6-1H,4H-Tetrahydro-8-methylquinolizino-[9,9a,1-gh]-coumarin);
- Coumarin 152A (7-Diethylamino-4-trifluormethylcoumarin);
- Coumarin 152 (7-Dimethylamino-4-trifluormethylcoumarin);
- Coumarin 151 (7-Amino-4-trifluormethylcoumarin);
- Coumarin 6H (2,3,5,6-1H,4H-Tetrahydroquinolizino-[9,9a,1-gh]coumarin);
- Coumarin 307 (7-Ethylamino-6-methyl-4-trifluormethylcoumarin);
- Coumarin 500 (7-Ethylamino-4-trifluormethylcoumarin);
- Coumarin 314 (2,3,5,6-1H,4H-Tetrahydro-9-carboethoxyquinolizino-[9,9a,1-gh]coumarin);
- Coumarin 510 (2,3,5,6-1H,4H-Tetrahydro-9-(3-pyridyl)-quinolizino-[9,9a,1-gh]coumarin);
- Coumarin 30 (3-2'-N-Methylbenzimidazolyl)-7-N,N-diethylaminocoumarin);
- Coumarin 552 (N-Methyl-4-trifluormethylpiperidino-[3,2-g]-coumarin);
- Coumarin 6 (3-(2'-Benzothiazolyl)-7-diethylaminocoumarin); and
- Coumarin 153 (2,3,5,6-1H,4H-Tetrahydro-8-trifluormethylquinolizino-9,9a,1-gh]coumarin).

Rhodamines may also be useful as fluorescent moieties. Rhodamine dyes based upon the fluorine molecule having a base molecule structure as:

and include the following examples:
- Rhodamine 110 (o-(6-Amino-3-imino-3H-xanthen-9-yl)-benzoic acid);
- Rhodamine 19 (Benzoic Acid, 2-[6-(ethylamino)-3-(ethylimino)-2,7-dimethyl-3H-xanthen-9-yl],perchlorate);
- Rhodamine 6G (Benzoic Acid, 2-[6-(ethylamino)-3-(ethylimino)-2,7-dimethyl-3H-xanthen-9-yl]-ethylester, monohydrochloride);
- Rhodamine B (2-[6-(Diethylamino)-3-(diethylimino)-3H-xanthen-9-yl]benzoic acid);
- Rhodamine 101 (8-(2-Carboxyphenyl)-2,3,5,6,11,12,14,15-octahydro-1H,4H,10H,13H-diquinolizino[9,9a,1-bc:9',9a', 1-hi]xanthylium Perchlorate).

Fluoresceins may also be useful as fluorescent moieties as shown below:

Examples include of fluoresceins include:
- Uranin (Disodium Fluorescein); and
- Fluorescein 27 (2,7-Dichlorofluorescein)

In short, the MS active, fluorescent rapid tagging glycan molecules described herein can utilize different other fluorescent moieties in place of the benzamide structure of Formula I and II.

For example, other fluorescent moieties that may be used together with a functional group and the MS active atom to produce an MS active, rapid tagging molecule include a biphenyl-phenyl, naphthyl-substituted oxadiazol moiety as shown immediately below.

Examples include:
- Butyl-PBD (2-(4-Biphenylyl)-5-(4-t-butylphenyl)-1,3,4-oxadiazol);
- PBD (2-(4-Biphenylyl)-5-phenyl-1,3,4-oxadiazol); and
- BBD (2,5-Bis-(4-biphenylyl)-1,3,4-oxadiazol).

Similarly, phenyl-substituted oxazols (shown immediately below) and furans (not shown) may be useful as the fluorescent moiety.

Examples of such moieties include:
- PPO (2,5-Diphenyloxazol);
- α-NPO (2-(1-Naphthyl)-5-phenyloxazol);
- BBO (2,5-Bis-(4-biphenylyl)-oxazol); and
- POPOP (1,4-Di[2-(5-phenyloxazolyl)]benzene).

In addition, other possible fluorescent moieties are shown below:

Ter and Quaterphenyls (shown above), where the examples include:
TMQ (3,3',2",3'"-Tetramethyl-p-quaterphenyl);
BMQ (2,2'"-Dimethyl-p-quaterphenyl);
DMQ (2-Methyl-5-t-butyl-p-quaterphenyl);
PQP (p-Quaterphenyl);
Polyphenyl 1 (p-Quaterphenyl-4-4'"-disulfonicacid Disodium salt);
Polyphenyl 2 (p-Quaterphenyl-4-4'"-disulfonicacid Dipotassium salt;
BiBuQ (4,4'"-Bis-(2-butyloctyloxy)-p-quaterphenyl);
BM-Terphenyl (2,2"-Dimethyl-p-terphenyl); and
PTP (p-Terphenyl).

Azaquinolone and carbostyryls (shown above), where the examples include:
Carbostyryl 7 (7-Amino-4-methylcarbostyryl);
Carbostyryl 3 (7-Dimethylamino-4-methylquinolon-2); and
Quinolon 390 (7-Dimethylamino-1-methyl-4-methoxy-8-azaquinolone-2).

Benzoxazoles and benofurans and benzothiazoles (shown above), where examples include:
DASBTI (2-(p-Dimethylaminostyryl)-benzothiazolyl-ethyl Iodide);
Coumarin 6 (3-(2'-Benzothiazolyl)-7-dimethylaminocoumarin);
Styryl 9M (2-(6-(4-Dimethylaminophenyl)-2,4-neopentylene-1,3,5-hexatrienyl)-3-methyl-benzothiazolium Perchlorate);
Styryl 15 (2-(6-(9-(2,3,6,7-Tetrahydro-1H,5H-benzo(i,j)-chinolizinium))-2,4-neopentylene-1,3,5-hexatrienyl)-3-methylbenzothiazolium Perchlorate);
Styryl 14 (2-(8-(4-p-Dimethylaminophenyl)-2,4-neopentylene-1,3,5,7-octatetraenyl)-3-methylbenzothiazolium Perchlorate);
Styryl 20 (2-(8-(9-(2,3,6,7-Tetrahydro-1H,5H-benzo(i,j)-chinolizinium))-2,4-neopentylene-1,3,5,7-octatraenyl)-3-methylbenzothiazolium Perchlorate);
Furan 1 (Benzofuran,2,2'-[1,1'-biphenyl]-4,4'-diyl-bis-tetrasulfonic acid (tetrasodium salt)); and
PBBO (2-(4-Biphenylyl)-6-phenylbenzoxazol-1,3).

Likewise, substituted stilbenes (phenyl, diphenyl, napthyl, etc. . . . ) shown immediately below might be used as the fluorescent moiety in an MS, rapid tagging fluorescent molecules. Substituted stilbenes have the base structure as follows:

Examples of substituted stilbenes (shown above) include:
DPS (4,4'-Diphenylstilbene);
Stilbene 1 ([1,1'-Biphenyl]-4-sulfonic acid, 4',4"-1,2-ethene-diylbis-, dipotassium salt); and
Stilbene 3 (2,2'-([1,1'-Biphenyl]-4,4'-diyldi-2,1-ethenediyl)-bis-benzenesulfonic acid disodium salt).

Likewise, as noted above, fluoro/rhodamine moieties (shown below) may be used as the fluorescent moiety:

An example is Fluorol 7GA (2-Butyl-6-(butylamino)-1H-benz[de]isoquinoline-1,3(2H)-dione).

Sulforhodamine dyes are also useful in connection with the molecules presented herein. Sulforhodamine dyes have a base molecule structure as follows:

Here, examples include:
Sulforhodamine B (Ethanaminium, N-[(6-diethylamino)-9-(2,4-disulfophenyl)-3H-xanthen-3-ylidene]-N-ethyl-hydroxid, inner salt, sodium salt); and
Sulforhodamine 101 (8-(2,4-Disulfophenyl)-2,3,5,6,11,12,14,15-octahydro-1H,4H,10H,13H-diquinolizino[9,9a,1-bc:9',9a',1-hi]xanthenes).

Pyrromethenes could also serve as the fluorescent moiety in the MS active rapid tagging molecules having the general structure below:

Examples of pyrromethenes include:
Pyrromethene 546 (1,3,5,7,8-pentamethylpyrromethenedifluoroborate complex);
Pyrromethene 556 (Disodium-1,3,5,7,8-pentamethylpyrromethene-2,6-disulfonate-difluoroborate complex);
Pyrromethene 567 (2,6-Diethyl-1,3,5,7,8-pentamethylpyrromethenedifluoroborate complex);
Pyrromethene 580 (2,6-Di-n-butyl-1,3,5,7,8-pentamethylpyrromethenedifluoroborate complex);
Pyrromethene 597 (2,6-Di-t-butyl-1,3,5,7,8-pentamethylpyrromethenedifluoroborate complex); and

Pyrromethene 650 (8-Cyano-1,2,3,5,6,7-hexamethylpyrromethenedifluoroborate complex).

Furthermore, phenoxazonium (shown immediately below) and phenoxazine may also be useful fluorescent moieties:

Examples of these fluorescent moieties include:
- Cresyl Violet (5,9-Diaminobenzo[a]phenoxazonium Perchlorate);
- Nile Blue (5-Amino-9-diethyliminobenzo[a]phenoxazonium Perchlorate);
- Oxazine 170 (9-Ethylamine-5-ethylimino-10-methyl-5H-benzo[a]phenoxazonium Perchlorate); and
- Oxazine 1 (3-Diethylamino-7-diethyliminophenoxazonium Perchlorate).

Pyrene-derivatives compose another class of fluorescent moieties that may be useful in connection with the molecules presented herein. Pyrene dyes are based upon the following basic structure:

Examples of pyrene-derivatives include:
- N-(1-pyrene)maleimide; and
- Pyranine (trisodium 8-hydroxypyrene-1,3,6-trisulfonate)

The fluorescent molecules and other fluorophores can be used.

Ideally, fluorescent molecules are those molecules that produce a fluorescent signal in the range of about 300 to 700 nanometers. Examples include rhodamines and coumarins.

Reactive functional groups can include succidimidylcarbamate and isocynate.

The present molecules can have heterocyclic aromatic groups that exhibit a higher fluorescence quantum yield that that of carbocyclic aromatics used as tags. Nimura et al Anal. Chem. 58, 2372 (1986). This increase in the fluorescence quantum yield of the tag provides an increase in the sensitivity of the tagged amine. For some of the heterocyclic molecules, the emission maximum of an amine compound derivatized with the reactive group is at a significantly different wavelength than the emission maximum of the free heterocyclic amine. The wavelength shift has very significant implications for fluorescence detection of tagged amines. Furthermore, since the observed fluorescence is predominantly from the derivative, background noise is eliminated or reduced and a more sensitive assay obtained.

Potential Synthetic Route to Procainamide Derivative.

Sample Preparation

The molecules provided herein do not provide a workaround for proper sample preparation. To obtain high quality mass spectra, the condition of the sample is of critical importance. Compounds other than the analyte will generally have an adverse effect on ion yield and must be removed. Indeed, while small amounts of sodium are essential for ionization by MALDI, carbohydrates are particularly susceptible to the effects of salts. Moreover, many carbohydrates occur as mixtures. Therefore it is important to ensure that isolation and purification techniques do not cause fractionation of the sample with a loss of quantitative information. Exemplary is sialic acids which often are lost from glycoproteins when pH is too low or sample temperature too high.

Example I

Preparation of 2,5-dioxopyrrolidin-1-yl (4-((2-(diethylamino)ethyl)carbamoyl)phenyl)carbamate 2.6 g of procainamide was added to 47 g of dry acetonitrile in a dry 100 mL Erlenmeyer flask equipped with a stir bar, and allowed to dissolve. In a separate 1 L flask equipped with a dropping funnel and a stir bar, 3.2 g of N,N-disuccinimidylcarbonate (DSC) was dissolved in 417 g of dry acetonitrile, and the system was purged with $N_2$. The solution of procainamide was then transferred to the dropping funnel, and added dropwise to the DSC solution over the course of 1 hour. The solution was then allowed to stir for 4 hours. At this point, the solvent was removed, and the product was dried at room temperature under high vacuum.

Example II

Preparation of 2,5-dioxopyrrolidin-1-yl (4-((2-(diethylamino)ethyl)carbamoyl)phenyl)carbamate 8.2 g of procainamide was added to 50 mL of dry dichloromethane in a dry 100 mL Erlenmeyer flask equipped with a stir bar, and allowed to dissolve. In a separate 1 L flask equipped with a dropping funnel and a stir bar, 10.1 g of N,N-disuccinimidylcarbonate (DSC) was mixed with 400 mL of dry dichloromethane, and the system was purged with N₂. The solution of procainamide was then transferred to the dropping funnel, and added dropwise to the DSC solution over the course of 1 hour. The solution was then allowed to stir for 4 hours. At this point, the desired product was removed from the mother liquor by filtration, then dried at room temperature under high vacuum.

Example III

Tagging of N-Linked Glycans Released from Herceptin

N-linked glycans were released from 0.8 µg of Herceptin using standard PNGase F protocols prior to labeling with 2,5-dioxopyrrolidin-1-yl (4-((2-(diethylamino)ethyl)carbamoyl)phenyl)carbamate. 2,5-dioxopyrrolidin-1-yl (4-((2-(diethylamino)ethyl)carbamoyl)phenyl)carbamate was solubilized in dry (water free) acetonitrile to a final concentration of 45 µg/µl. 10 µl to this solution was then added to the to the released glycan sample. This mixture was left at room temperature for 5 minutes. The labeled sample was then lyophilized using a speed vac and reconstituted in 60% acetonitrile/water solution prior to chromatographic separation using a HILIC LC method and analysis by fluorescence and MS detection, as shown in FIGS. 1 and 2.

Prophetic Example IV

Prophetic Example V

Synthesis II

N,N disuccinimidylcarbonate +

Synthesis I a) R = C
b) R = N

We claim:

1. A compound of the structural formula:

2. A compound of the structural formula:

3. A compound of Formula IV:

wherein
X=C or N
R¹ is O=C=N— or

R² is independently selected from —H, —C₁-C₈ alkyl, —C₁-C₈ cycloalkyl, halo, dialkylamino, CH₂-dialkylamino, aminocarbonyl, alkoxycarbonyl, or alkoxy, but not Cl or O=C=N—; and
R³ and R⁴ are independently selected from —H, alkyl, alkyl amino, alkylsulfonic acid, alkyl phosphonic acid, wherein either R³ or R⁴ is alkylamino, alkyl phosphonic acid, or alkylsulfonic acid.

4. A compound of Formula V:

wherein
m=0-9;
n=0-9;
X=C or N
R¹ is O=C=N—, S=C=N—, or

R² is independently selected from methylene, substituted nitrogen, oxygen, carbonyl, amide, ester, sulfur, sulfoxide, or sulfone;
R³ and R⁴ are independently selected from —H, alkyl, alkyl amino, alkylsulfonic acid, alkyl phosphonic acid, wherein either R³ or R⁴ is alkylamino, alkyl phosphonic acid, or alkylsulfonic acid; and
R⁵ is independently selected from —H, —C₁-C₈ alkyl, —C₁-C₈ cycloalkyl, halo, dialkylamino, CH₂-dialkylamino, aminocarbonyl, alkoxycarbonyl, or alkoxy, but not Cl when R¹ is O=C=N—, and when R¹ is S=C=N, R⁵ is H.

5. A method for analyzing a glycan, an amino acid or an amine containing compound in a sample by means of liquid chromatography and mass spectrometry comprising labeling the glycan, the amino acid or the amine containing compound in the sample by reacting with a compound of the structural formula:

for a time and under conditions suitable to facilitate the labeling; ; and subjecting the labeled compound to liquid chromatograph and mass spectrometry.

6. A method for analyzing a glycan, an amino acid or an amine containing compound in a sample by means of liquid chromatography and mass spectrometry comprising labeling the glycan, the amino acid or the amine containing compound in the sample by reacting with a compound of the structural formula for a time and under conditions suitable to facilitate the labeling; ; and subjecting the labeled compound to liquid chromatograph and mass spectrometry.

7. A method for analyzing a glycan, an amino acid or an amine containing compound in a sample by means of liquid chromatography and mass spectrometry comprising labeling the glycan, the amino acid or the amine containing compound in the sample by reacting with a compound according to claim 3 for a time and under conditions suitable to facilitate the labeling and subjecting the labeled compound to liquid chromatograph and mass spectrometry.

8. A method for analyzing a glycan, an amino acid or an amine containing compound in a sample by means of liquid chromatography and mass spectrometry comprising labeling the glycan, the amino acid or the amine containing compound in the sample by reacting with a compound according to claim 4 for a time and under conditions suitable to facilitate the labeling and subjecting the labeled compound to liquid chromatograph and mass spectrometry.

9. A method for rapid tagging of a glycan, an amino acid or an amine containing compound comprising reacting the glycan, the amino acid or the amine containing compound with the compound of the structural formula:

10. A method for rapid tagging of a glycan, an amino acid or an amine containing compound comprising reacting the glycan, the amino acid or the amine containing compound with the compound of the structural formula:

11. A method for rapid tagging of a glycan, an amino acid or an amine containing compound comprising reacting the glycan, the amino acid or the amine containing compound with the compound of claim 3.

12. A method for rapid tagging of a glycan, an amino acid or an amine containing compound comprising reacting the glycan, the amino acid or the amine containing compound with the compound of claim 4.

* * * * *